United States Patent
Graveley et al.

(10) Patent No.: US 12,396,801 B2
(45) Date of Patent: Aug. 26, 2025

(54) MEDICAL DEVICE ASSEMBLIES AND COMPONENTS

(71) Applicant: Boston Scientific Scimed, Inc., Maple Grove, MN (US)

(72) Inventors: Andrew Graveley, Shoreview, MN (US); Nathaniel Behning, Lino Lakes, MN (US); Kyle True, Minneapolis, MN (US); Bradley Swehla, Eagan, MN (US); Daniel Foster, Lino Lakes, MN (US); Steven Meyer, Lake Elmo, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 156 days.

(21) Appl. No.: 18/307,365

(22) Filed: Apr. 26, 2023

(65) Prior Publication Data
US 2023/0355318 A1 Nov. 9, 2023

Related U.S. Application Data

(60) Provisional application No. 63/364,062, filed on May 3, 2022.

(51) Int. Cl.
*A61B 34/20* (2016.01)
*A61B 1/05* (2006.01)
*A61B 5/06* (2006.01)

(52) U.S. Cl.
CPC ............... *A61B 34/20* (2016.02); *A61B 1/05* (2013.01); *A61B 5/065* (2013.01); *A61B 2034/2051* (2016.02)

(58) Field of Classification Search
CPC ..... A61B 1/00097; A61B 1/05; A61B 1/0676; A61B 1/2676; A61B 2034/2051; A61B 2562/0223; A61B 34/20; A61B 5/062; A61B 5/065
See application file for complete search history.

(56) References Cited

U.S. PATENT DOCUMENTS

| 10,782,114 B2 | 9/2020 | Hein et al. |
| 2001/0026222 A1* | 10/2001 | Canady, Jr. ............ A61B 5/113 340/572.1 |
| 2009/0306476 A1 | 12/2009 | Banik et al. |

(Continued)

FOREIGN PATENT DOCUMENTS

CN 208837903 U * 5/2019 ......... G02B 6/02147

OTHER PUBLICATIONS

Translated Suzhou CN 208837903 U (Year: 2019).*
International Search Report and Written Opinion in PCT/US2023/019956, mailed Jul. 27, 2023 (11 pages).

*Primary Examiner* — Anne M Kozak
*Assistant Examiner* — Brooke Lyn Klein
(74) *Attorney, Agent, or Firm* — Bookoff McAndrews, PLLC

(57) ABSTRACT

A medical assembly may comprise: a substrate configured to be disposed in a body at a distal tip of a medical device; and a position sensing system, including a magnetic field sensor mounted to the substrate. The magnetic field sensor may be configured to provide a signal that indicates a position or orientation of the distal tip of the medical device. The medical assembly may further comprise at least one camera mounted to the substrate; and at least one lighting element mounted to the substrate.

20 Claims, 7 Drawing Sheets

(56) References Cited

U.S. PATENT DOCUMENTS

| | | |
|---|---|---|
| 2017/0059361 A1 | 3/2017 | Nagarkar et al. |
| 2019/0217059 A1 | 7/2019 | Meyer et al. |
| 2020/0085283 A1* | 3/2020 | Salman .............. G02B 27/0006 |
| 2020/0107701 A1 | 4/2020 | Gliner et al. |
| 2021/0093223 A1 | 4/2021 | Kosel et al. |
| 2021/0127953 A1* | 5/2021 | Oyama ................ A61B 1/0676 |
| 2022/0257093 A1* | 8/2022 | Tarke ....................... A61B 1/32 |
| 2022/0395167 A1* | 12/2022 | Zhang ...................... A61B 1/05 |

* cited by examiner

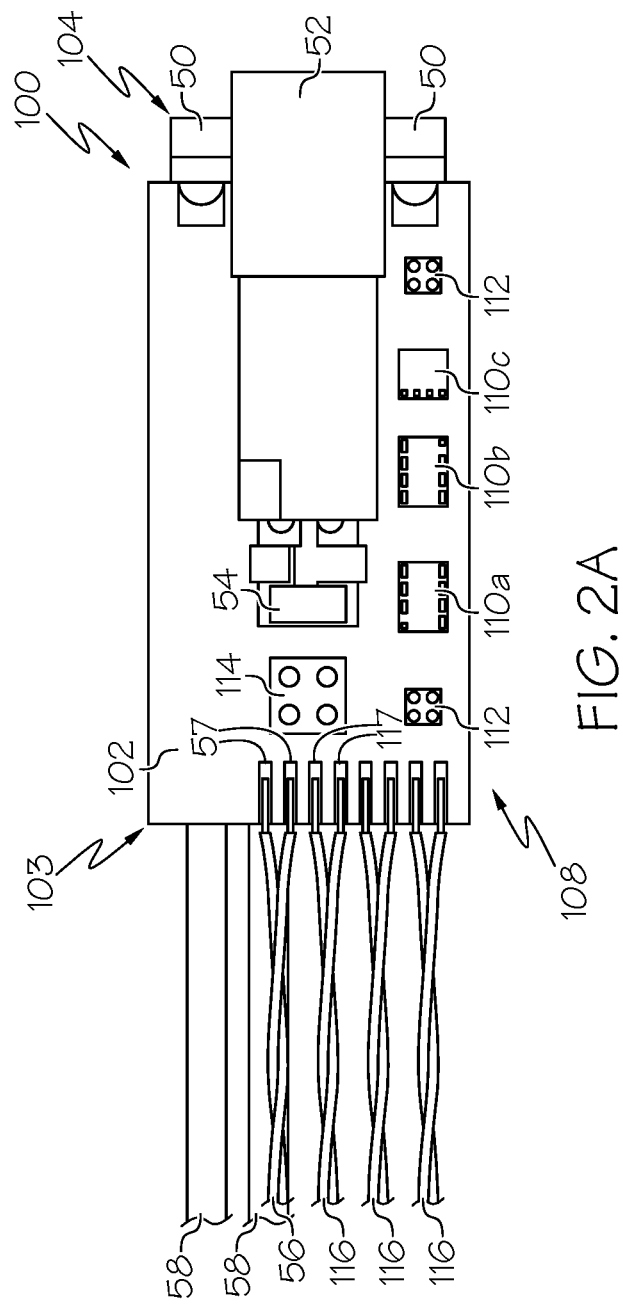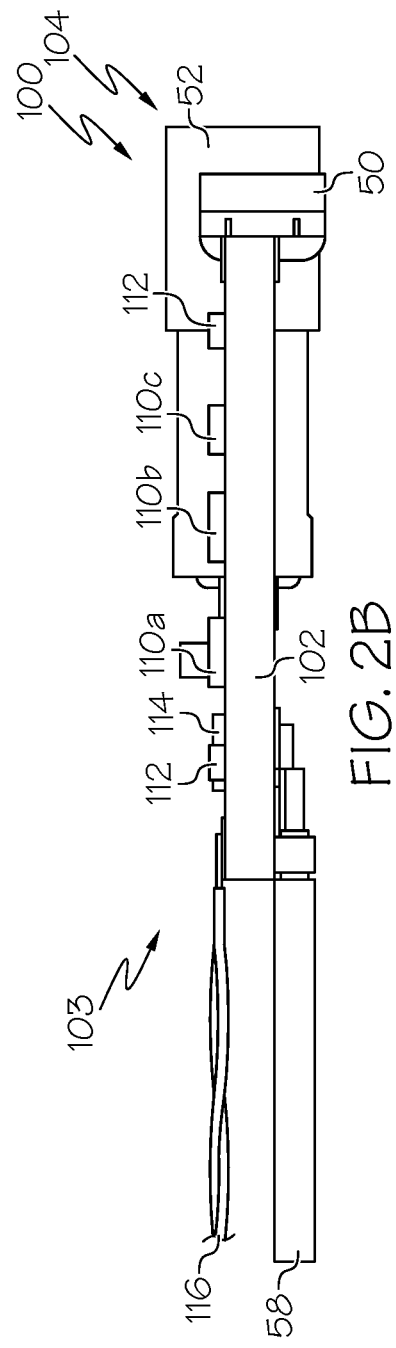
FIG. 2A
FIG. 2B

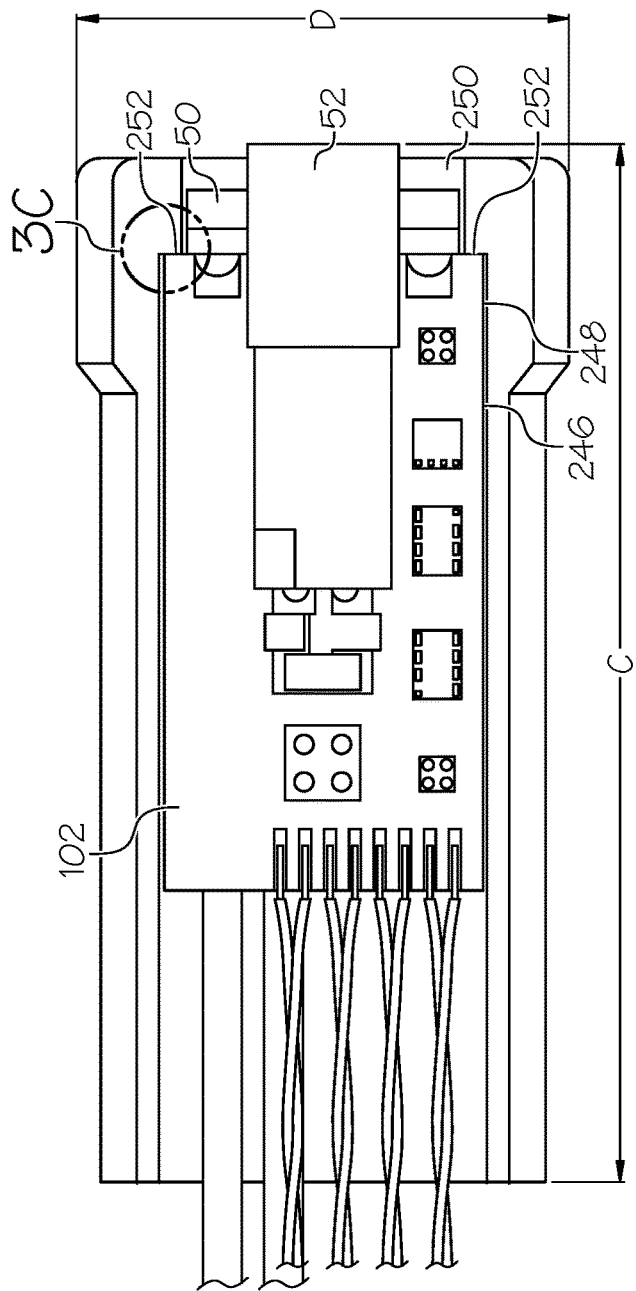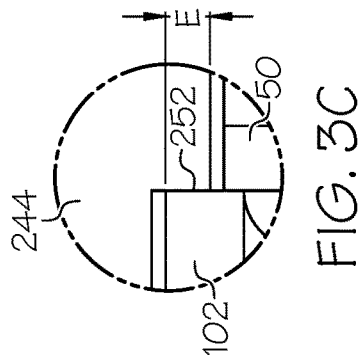
FIG. 3B
FIG. 3C

MEDICAL DEVICE ASSEMBLIES AND COMPONENTS

CROSS-REFERENCE TO RELATED APPLICATION(S)

This application claims the benefit of priority from U.S. Provisional Application No. 63/364,062, filed on May 3, 2022, which is incorporated by reference herein in its entirety.

TECHNICAL FIELD

The disclosure relates generally to devices, systems, and methods for medical device assemblies and components. More specifically, aspects of the disclosure pertain to devices, systems, and/or methods for electronic assemblies of medical devices, including position-tracking assemblies.

BACKGROUND

In a medical procedure, an operator may insert a medical device, such as a bronchoscope or other type of scope, into a body lumen of a subject. The operator may navigate a distal tip of the medical device to a desired location of the subject's anatomy. Prior to the medical procedure, an area of interest in the patient's anatomy may be predefined. The operator may then attempt to navigate the medical device to that predefined area of interest. Such navigation may be challenging, particularly in tortuous passages or complicated areas of anatomy (e.g., the lungs). An imager (e.g., a camera) at a distal tip of the medical device may facilitate such navigation, but cannot provide information about areas past the walls of the body lumen. Effective navigation using only an imager may require high levels of skill, time, and/or effort.

An endoscopic robotic system may rely on position information for a distal tip of a medical device. Some robotic systems utilize position encoders in a motor system of the robotic system. Such sensors, however, do not provide useful information for a flexible tool (such as a bronchoscope, other type of scope, a biopsy tool for passing through a working channel of an endoscope, or another type of flexible tool). Therefore, a need exists for systems, devices, and/or methods for electronic assemblies or components of medical devices, including position-tracking assemblies or components.

SUMMARY

A medical assembly may comprise: a substrate configured to be disposed in a body at a distal tip of a medical device; and a position sensing system, including a magnetic field sensor mounted to the substrate. The magnetic field sensor may be configured to provide a signal that indicates a position or orientation of the distal tip of the medical device. The medical assembly may further comprise at least one camera mounted to the substrate; and at least one lighting element mounted to the substrate.

In any of the exemplary assemblies herein, the magnetic field sensor may include a magneto-resistive ("MR") sensor. The MR sensor may be a first MR sensor, and the position sensing system may further includes a second MR sensor and a third MR sensor. The first MR sensor may have a first primary sensing direction, the second MR sensor may have a second primary sensing direction, and the third MR sensor may have a third primary sensing direction. The first MR sensor and the second MR sensor may be arranged so that each of the first primary sensing direction and the second primary sensing direction is approximately parallel with a longitudinal axis of the substrate. The third TMR sensor may be arranged such that the third primary sensing direction is transverse to the longitudinal axis of the substrate. The position sensing system may be configured to measure at least five degrees of freedom. The first MR sensor, the second MR sensor, and the third MR sensor may collectively include at least one Wheatstone bridge configuration. The system may further comprise six wires in electrical connection with the position sensing system. The system may further comprise two wires in electrical connection with the at least one lighting element. Each of the six wires in electrical connection with the position sensing system and each of the two wires in electrical connection with the at least one lighting element may be connected to a first side of the substrate. The assembly may further comprise the body. The body may include a cavity configured to receive the substrate. The cavity may include a proximal portion and a distal portion. The distal portion may have a smaller width than the proximal portion. The width may be measured in a direction that is perpendicular to a longitudinal axis of the medical device and across a face of the substrate. The at least one camera and the at least one lighting element may be at least partially received within the distal portion of the cavity. The cavity may define a shoulder portion extending between the proximal portion of the cavity and the distal portion of the cavity. A distal surface of the substrate may be configured to contact the shoulder portion. A distal opening of the cavity may have a contoured shape that complements the at least one camera and the at least one lighting element.

In another example, a medical assembly, may comprise: a body at a distal tip of a medical device. The body may define a cavity. The assembly may further comprise a substrate disposed in the cavity, the substrate having mounted thereto: a magnetic field sensor configured to provide a signal that indicates a position or orientation of the distal tip of the medical device. The assembly may further comprise at least one camera.

Any of the exemplary assemblies disclosed herein may include any of the following features. The magnetic field sensor may be a first MR sensor. The substrate may have mounted thereto a second MR sensor and a third MR sensor. The cavity may include a proximal portion and a distal portion. The distal portion may have a smaller width than the proximal portion. The width may be measured in a direction that is perpendicular to a longitudinal axis of the medical device and across a face of the substrate. The at least one camera may be at least partially received within the distal portion of the cavity.

In another example, a medical assembly may comprise: a body at a distal tip of a medical device. The body may define a cavity. The assembly may further comprise a substrate disposed in the cavity; and a magnetic field sensor mounted to the substrate. The magnetic field sensor may be configured to provide a signal that indicates a position or orientation of the distal tip of the medical device. The substrate may include a plurality of contact pads disposed on a first side of the substrate. At least a first of the plurality of contact pads may be configured to provide an electrical connection between (a) a first conductor and (b) the magnetic field sensor. At least a second of the plurality of contact pads may be configured to provide an electrical connection between (c) a second conductor and (d) a camera or a lighting element.

Any of the assemblies disclosed herein may have any of the following features. The magnetic field sensor may include an MR sensor.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The term "distal" refers to a direction away from an operator/toward a treatment site, and the term "proximal" refers to a direction toward an operator. The term "approximately," or like terms (e.g., "substantially"), includes values+/−10% of a stated value.

BRIEF DESCRIPTION OF THE DRAWINGS

The accompanying drawings, which are incorporated in and constitute a part of this specification, illustrate examples of this disclosure and together with the description, serve to explain the principles of the disclosure.

FIGS. 2A-2C depict an exemplary distal component assembly for use with the medical device of FIGS. 1A and 1B.

FIGS. 3A-3F depict the distal component assembly of FIGS. 2A-2C combined with an exemplary distal tip body of the medical device of FIGS. 1A and 1B.

DETAILED DESCRIPTION

Figure 1A:
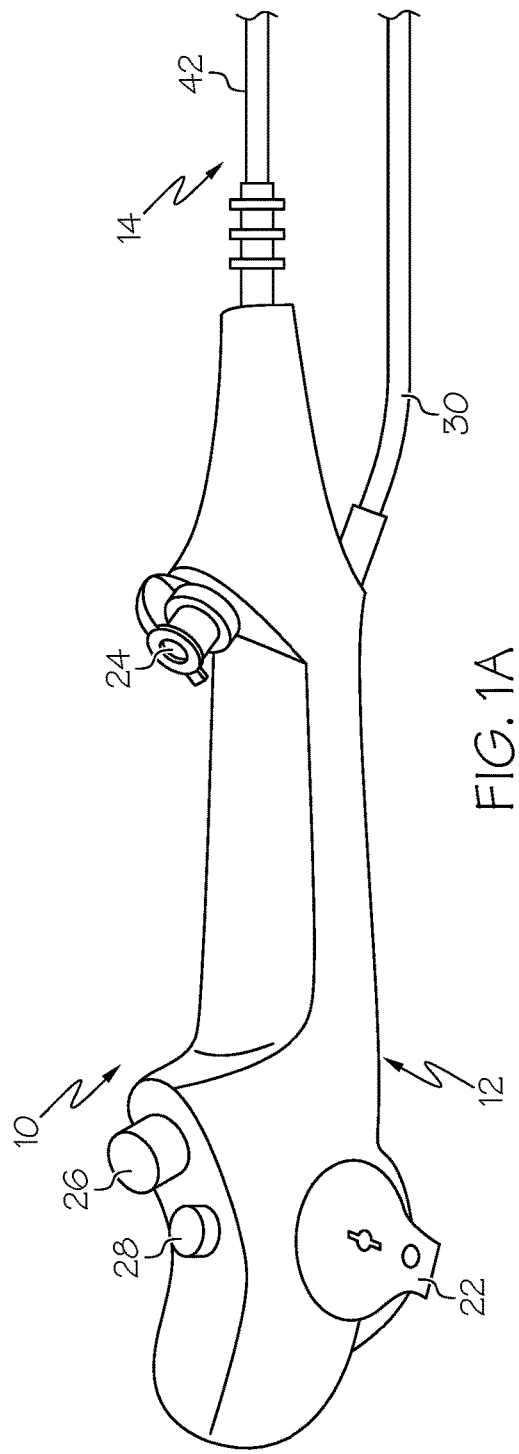
FIGS. 1A and 1B depict an exemplary medical device.

Robotic-assisted and electromagnetic ("EM")-navigated medical procedures may utilize EM tracking to provide information regarding a position and/or orientation of a medical device within a subject's anatomy. When a medical device has a camera but does not utilize EM tracking, an operator is unable to see past an endothelial wall, or other type of wall or body structure. With EM tracking, position and/or orientation information may be fused with imaging (e.g., three-dimensional ("3D") imaging) performed before a procedure. An operator may have greater information about the anatomy near the medical device, which a camera alone may be unable to visualize (including anatomy outside of a body lumen in which the medical device is disposed). Furthermore, pre-procedure images may be used to automatically segment a mesh of the anatomy so as to provide a map (e.g., a 3D map) to track the medical device in real time. Such real-time tracking may help to decrease the amount of time, skill, and/or effort required to reach a target anatomy. In the absence of pre-procedure images, EM sensors may enable software to track the position and movements of the medical device in order to generate a map (e.g., a 3D map) in real time, during a procedure. The generated map may guide the medical device (and any EM-enabled accessories) through the subject's anatomy. Unlike traditional robotic systems, which may rely on position encoders in a motor system to provide necessary position information for a tip of a medical device, such as a rigid medical device or a rigid portion of a medical device, EM-based systems may provide position information for flexible medical devices.

A single circuit board at a distal end of a medical device may include elements such as position-sensing systems, imaging elements, and lighting elements. The position-sensing elements may enable EM tracking of the medical device. For example, a position-sensing system may include one or more tunneling magnetoresistance ("TMR") sensors (i.e., TMR elements), one or more diodes (e.g., two diodes), and/or one or more capacitors (e.g., one capacitor). Imaging elements may include one or more cameras. Lighting elements may include one or more (e.g., two) light emitting diodes ("LEDs") or fiber optic light guides. Wires, cables, or other conductors for carrying power and/or signals to the elements of the circuit board may extend proximally from the circuit board, toward a proximal end of the medical device. Various elements may be arranged on the circuit board to arrange for efficient connections between the circuit board and the conductors carrying power and/or signals.

A distal tip body (e.g., a housing) of the medical device may be configured to receive the circuit board. Inclusion of position sensing elements, imaging elements, and/or lighting elements on a single circuit board may facilitate cost-effective manufacturing by, for example, reducing a number of steps to assemble the medical device, reducing a likelihood of errors in assembly, and/or reducing waste. For example, rather than separately assembling lighting elements, imaging elements, and/or sensing elements on or within a distal tip body, all of these elements (and the conductors providing power and/or signals thereto) may be fitted to the distal tip body in a single step.

Figure 1B:
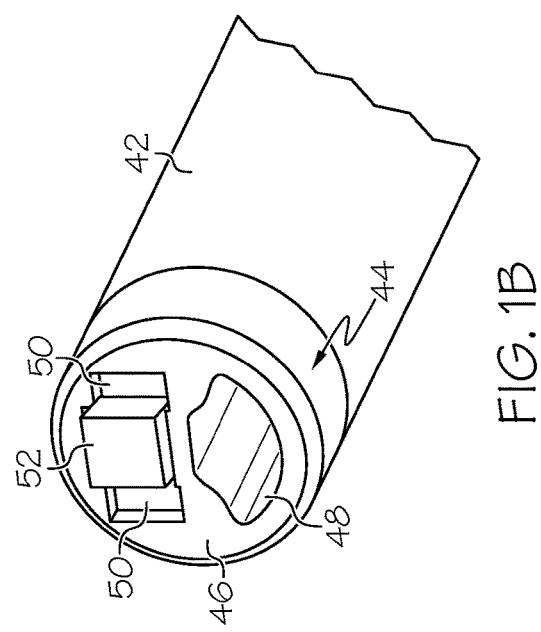

FIGS. 1A and 1B depict aspects of an exemplary medical device 10. FIG. 1A depicts a proximal portion of medical device 10. FIG. 1B depicts a distal tip 44 of medical device 10. Medical device 10 may include a handle portion 12 for gripping and operation by an operator, and an insertion portion 14 for at least partial insertion into a body (e.g., a body lumen) of a subject. As shown in FIGS. 1A and 1B, medical device 10 may include a bronchoscope. Although the disclosure may refer at different points to a bronchoscope or an endoscope, it will be appreciated that, unless otherwise specified, duodenoscopes, endoscopes, gastroscopes, endoscopic ultrasonography ("EUS") scopes, colonoscopes, ureteroscopes, bronchoscopes, laparoscopes, cytoscopes, aspiration scopes, sheaths, catheters, or any other suitable delivery device or medical device may be used in connection with the elements and assemblies described herein.

Handle portion 12 may include a lever 22, for example, on a proximal portion of handle portion 12. Lever 22 may help to facilitate articulation/steering of insertion portion 14, including distal tip 44. Although lever 22 is depicted in FIG. 1A, it will be appreciated that any suitable actuator(s) may be used in addition to or in place of lever 22, such as one or more knobs, buttons, sliders, or joysticks. A port 24 of handle portion 12 (e.g., on a proximal portion of handle portion 12) may provide access to a lumen or working channel of medical device 10. An operator may insert an instrument or other device into port 24 and may extend the instrument or other device distally through the working channel. The working channel may extend longitudinally through a length of insertion portion 14. Handle portion 12 may also include a suction valve 26, for example, on a proximal portion of handle portion 12 and on an opposing side from lever 22. An operator may connect suction valve 26 to a source of suction, and may operate suction valve 26 to generate suction through insertion portion 14 (e.g., through the working channel). Handle portion 12 may additionally or alternatively include other types of valves, such as air and/or water valves, or valves that perform a combination of functions. An image capture button 28 of handle portion 12 may enable an operator to capture a still image from a camera 52 (shown in FIG. 1B and described in further detail below) during a procedure. Image capture button 28 may be positioned on a proximal portion of handle portion 12, for example, adjacent suction valve 26. Additionally or alternatively, image capture button 28 may enable an operator to capture video or to perform other functions to control medical device 10. An umbilicus 30 may extend from handle portion 12 (e.g., from a distal portion of handle portion 12) and may carry wires, cables, and/or conduits for providing, for example, power, signals, or fluids to or from handle portion 12. For example, umbilicus 30 may connect handle portion 12 to one or more user interfaces, monitors, displays, etc.

Insertion portion 14 may include a shaft 42 extending distally from handle portion 12. Shaft 42 may have any suitable properties. For example, shaft 42 may be flexible and may have wires, tubes, or other features passing therethrough. Distal tip 44 of medical device 10, depicted in FIG. 1B, may be disposed at a distal end of shaft 42. As shown in FIG. 1B, distal tip 44 may include a distalmost face 46. Distalmost face 46 may define a working channel opening 48. The working channel may extend between port 24 and working channel opening 48, such that instruments or other devices may be passed through port 24, through the working channel, and out of working channel opening 48. An instrument extending distally of working channel opening 48 may be used to perform a medical procedure on a subject.

Distal tip 44 may also include imaging components, such as one or more lighting elements 50 and a camera 52. Although two lighting elements 50 and one camera 52 are depicted in FIG. 1B, it will be appreciated that alternative numbers of lighting elements 50 and camera 52 may be utilized. Alternatively, lighting elements 50 and camera 52 may be combined into a single device. Lighting elements 50 may include LEDs or any suitable alternative light source. Camera 52 may be configured to take video and/or still images. Camera 52 may provide a signal to a monitor (not shown), so that an operator may view a visual image provided by camera 52 while navigating medical device 10 through a body of a subject.

As depicted in FIG. 1B and described above, medical device 10 may be "forward-facing." In other words, features of distal tip 44 (e.g., working channel opening 48, lighting elements 50, and camera 52) may face distally (i.e., forward of distalmost face 46. This disclosure also encompasses other configurations of distal tip 44. For example, medical device 10 may be "side-facing." In a side-facing embodiment, working channel opening 48, lighting elements 50, and/or camera 52 may be disposed on a radially outer side of distal tip 44, so that they point in a radially outward direction, approximately perpendicularly to a longitudinal axis of insertion portion 14.

Figure 2C:
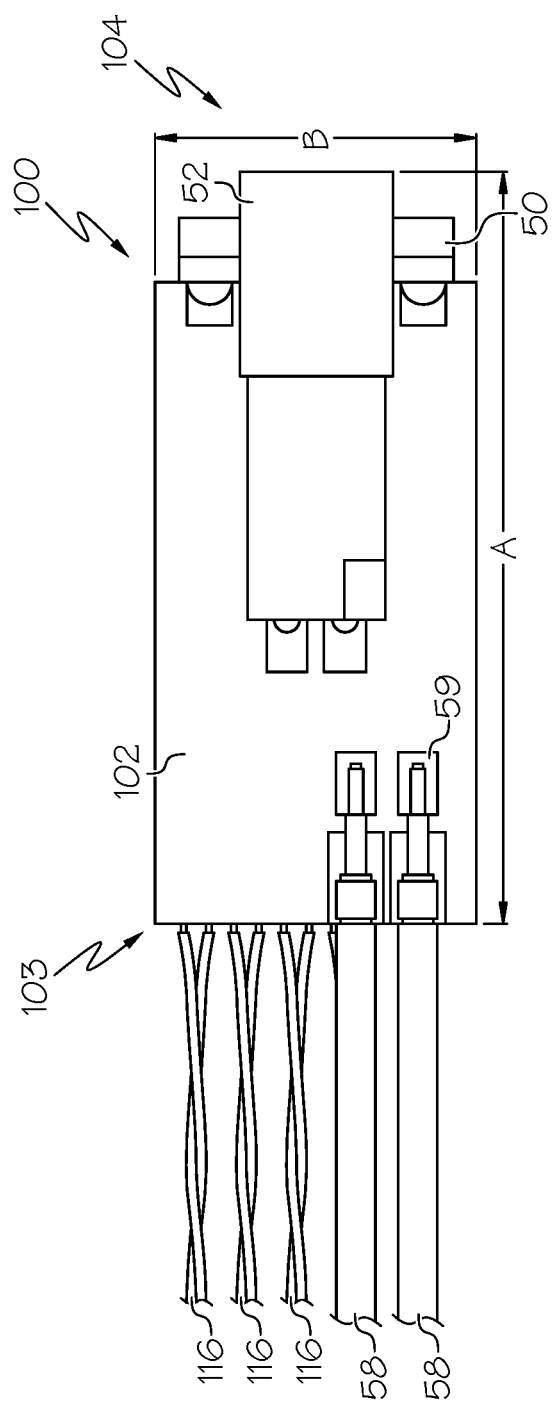

FIGS. 2A-2C depict different views of a distal component assembly 100, which may constitute or be included in a medical assembly. As discussed in further detail below, with reference to FIGS. 3A and 3B, distal component assembly 100 may be disposed in distal tip 44 of medical device 10. Distal component assembly 100 may include a substrate 102 (e.g., a circuit board or other type of board). Substrate 102 may include, for example, a rigid or flexible printed circuit board and may include one or more layers. In one example, substrate 102 is rigid and includes multiple layers. A distal end 104 of distal component assembly 100 may be a rightmost side in FIGS. 2A-2C. A proximal end 103 of distal component assembly 100 may be a leftmost side in FIGS. 2A-2C. A first face (shown in plan view in FIG. 2A) and a second face (opposite of the first face and shown in plan view in FIG. 2C) of substrate 102 may face radially outward when distal component assembly 100 is assembled in distal tip 44 of medical device 10. The view of FIG. 2C is rotated 180 degrees relative to the view of FIG. 2A. FIG. 2B shows a view that is rotated by 90 degrees from the views of FIGS. 2A and 2C. In FIG. 2B, the first face of substrate 102 faces upward and the second face of substrate 102 faces downward. Distal component assembly 100 may have a length (along a longitudinal axis of distal tip 44 and device 10) of approximately 0.1" to approximately 0.3" (e.g., approximately 0.237"). Distal component assembly 100 may have a width (across the first or second face, perpendicularly to the longitudinal axis) of approximately 0.09" to approximately 0.12" (e.g., approximately 0.101").

Lighting elements 50 and camera 52 may be mounted to substrate 102. As shown in FIGS. 2A-2C, distal ends of lighting elements 50 and camera 52 may extend distally of a distal end of substrate 102. In some examples, lighting elements 50 may be mounted to a distal edge of substrate 102. As shown particularly in FIG. 2A, a portion of lighting elements 50 may contact the distal edge of substrate 102. Other portions of lighting elements 50 may contact the first and second faces of substrate 102. In some examples, lighting elements 50 may be bonded to substrate 102 (e.g., directly to substrate 102) with a transparent material (e.g., adhesive or other material) assembled atop lighting elements 50. In some aspects, the transparent material may act as a light guide to direct or re-direct light from lighting elements 50 to be in front of (i.e., distal to) camera 52.

Substrate 102 may include a notch or opening formed therein for receiving camera 52 (or other components of distal component assembly 100). Camera 52 may extend distally beyond lighting elements 50 and may extend radially outward from the first and second faces of substrate 102. Camera 52 may extend further radially outward than lighting elements 50. Camera 52 may include a camera capacitor 54 or any other suitable accessory components, which may be formed integrally with camera 52 or as separate element(s).

Camera 52 may be disposed approximately centrally along the width of substrate 102. Lighting elements 50 may be arranged symmetrically on either side of camera 52. Lighting elements 50 may be directly adjacent to (contacting) camera 52, or there may be a gap between camera 52 and lighting elements 50. A portion of substrate 102 may extend width-wise past each of lighting elements 50, such that substrate 102 is the widest part of distal component assembly 100. An amount of substrate 102 that extends width-wise past each of lighting elements 50 may be approximately equal, such that the distal end of distal component assembly is approximately symmetrical.

A twisted pair of wires 56 may provide power to lighting elements 50. Each of wires 56 may electrically connect to a contact pad 57 on a proximal end of the first side of substrate 102 so that wires 56 are in electrical connection with lighting elements 50. Electrical traces or wires may extend from the contact pad 57 to lighting elements 50. Including lighting elements 50 on substrate 102 may allow fewer wires to be used than in other systems. For example, absent substrate 102, multiple wires may be required to power multiple separate lighting elements 50. Using one set of twisted wires 56, connected to substrate 102, may save space in shaft 42 and/or reduce costs as compared to using multiple wires or cables (e.g., multiple twin-ax wires) to power each of lighting elements 50. Although shields are not depicted in FIGS. 2A-2C, one or more shields may be positioned around wires 56.

One or more cables 58 may transmit power and signals to and from camera 52. Cables 58 may include, for example, micro-coaxial cables or other suitable cables or wires. As shown in FIGS. 2A and 2C, distal component assembly 100 may include two cables 58. The number of cables 58 shown in FIGS. 2A and 2C is merely exemplary, and other suitable numbers of cables may be utilized. As shown particularly in FIG. 2C, distal ends of each of cables 58 may be fixed to one or more of contact pads 59 (e.g., via bonding or soldering) on a proximal end of the second side of substrate 102 to provide an electrical connection between cables 58 and camera 52 (via, e.g., electrical traces or wires between the contact pads 59 and camera 52). As shown in FIGS. 2A-2C, the contact pads 59 for attaching to cables 58 and the contact pads 57 for attaching to wires 56 may be on opposite sides of substrate 102. In an example, contact pads 59 for attaching to cables 58 may be approximately opposite to contact pads 57 for attaching to cables 58. For example, contact pads 59 and contact pads 57 may be on opposite faces of substrate 102 but may be directly opposite one another, to save space on substrate 102. However, such an arrangement is merely exemplary and other arrangements may be utilized. For example, wires 56 may connect to contact pads 57 on a same side of substrate 102 as the contact pads 59 for connecting to cables 58.

In alternatives, the twisted pair of wires 56 may be replaced with twin-axial wires or cables (such as micro-coaxial cables) to allow soldering or bonding of conductors powering lighting elements 50 with the same process as used to attach cables 58 and/or to reduce noise from electromagnetic interference.

Elements of a position sensing system 108 may also be disposed on substrate 102. Position sensing system 108 may incorporate any of the features described in U.S. patent application Ser. No. 15/846,846, filed Dec. 19, 2017, issued as U.S. Pat. No. 10,782,114, on Sep. 22, 2020, the entirety of which is incorporated herein by reference. Position sensing system 108 may include one or more magnetic field sensors 110a, 110b, 110c disposed on substrate 102. For example, as shown in FIGS. 2A and 2B, three magnetic field sensors 110a, 110b, 110c may be disposed on substrate 102. Any alternative number of sensors may be utilized, and the three sensors 110a, 110b, 110c depicted are exemplary only. Magnetic field sensors 110a, 110b, 110c may include, for example, magneto-resistive elements, such as TMR elements, anisotropic-magneto-resistive sensing elements, giant magneto-resistive sensing elements, colossal magneto-resistive sensing elements, extraordinary magneto-resistive sensing elements, or semiconductor magneto-resistive elements. Additionally or alternatively, magnetic field sensors 110a, 110b, 110c may include one or more inductive sensors (e.g., a inductive coil sensors), planar coil sensors, spin Hall sensing elements (or other Hall sensing elements), or magnetic gradiometer(s), Although TMR sensors and properties of TMR sensors may be referred to herein, it will be appreciated that any type of magnetic field sensor may be utilized, including those listed above. Magnetic field sensors 110a, 110b, 110c may have any properties of magnetic field sensors (including, e.g., TMR sensors) known in the art. For example, magnetic field sensors 110a, 110b, 110c may include a fixed layer, a tunnel layer, and a free layer. A resistance may change when the free layer is aligned with the fixed layer.

In some examples, as shown in FIG. 2A, magnetic field sensors 110a, 110b, 110c may be arranged in a dual-axis, six-degree-of-freedom arrangement. In such an arrangement, two magnetic field sensors 110a, 110b may be oriented such that their primary sensing direction is aligned with (approximately parallel to) a longitudinal axis of device 10 (which is also a longitudinal axis of component assembly 100/substrate 102). A full-Wheatstone bridge configuration may be utilized by the two magnetic field sensors 110a, 110b. The third magnetic field sensor 110c may be arranged such that its primary sensing direction is transverse (e.g., approximately orthogonal/perpendicular) to the longitudinal axis. A half-Wheatstone bridge configuration may be utilized by magnetic field sensor 110c. The Wheatstone bridges may have any characteristics of Wheatstone bridges known in the art. Sensors 110a, 110b, 110c may detect an orientation/position of distal component assembly 100 and may transmit signals indicative of the orientation/position of distal component assembly 100. A controller (not shown) may receive the signals and may calculate positioning of distal component assembly 100 using the measurements from magnetic field sensors 110a, 110b, 110c across the primary sensing direction (from magnetic field sensors 110a, 110b) and the direction orthogonal to the primary sensing direction (from magnetic field sensor 110c).

Position sensing system 108 may also optionally include a capacitor 114 for reducing noise in a voltage supplying position sensing system 108. For example, capacitor 114 may function as a decoupling capacitor, acting as a low-pass filter for any electromagnetic interference ("EMI") on the supply voltage. Position sensing system 108 may also optionally include one or more diodes 112. Diodes 112 may provide high voltage protection, such as electrostatic discharge ("ESD") protection. Diodes 112 may prevent damage to magnetic sensors 110a, 110b, 110c from static discharge. Diodes 112 may additionally or alternatively provide protection to aspects of camera 52.

As shown particularly in FIG. 2A, each wire 116 of three pairs of twisted wires 116 may be electrically connected to contact pads 117 on the first side of substrate 102 (on the same side of substrate 102 as the contact pads 57 for wires 56). Wires and/or traces may electrically connect contact pads 117 and elements of position sensing system 108. In some configurations, contact pads 117 for electrically connecting to wires 116 may also be disposed on the same side of substrate 102 as the contact pads 59 for connecting to cables 58. Wires 116 may provide power to and/or signals from various aspects of position sensing system 108. The three pairs of twisted wires 116 may include six individual wires 116. Two of those wires 116 may be used to provide power to position sensing system 108. Two of the remaining four wires 116 may be connected to the full Wheatstone bridge of magnetic field sensors 110a, 110b. The remaining two wires may be connected to the half Wheatstone bridge of magnetic field sensor 110c. Although shields are not depicted in FIGS. 2A-2C, shields may be positioned around wires 116. In alternative examples, the twisted pair of wires 116 may be replaced with twin-axial wires or cables (such as micro-coaxial cables) to allow soldering or bonding of conductors powering position sensing system 108 with the same process as used to attach cables 58 and/or to reduce noise from electromagnetic interference.

Position sensing system 108 may have other configurations within the scope of the disclosure. For example, a tri-axis configuration may be utilized for magnetic field sensors 110a, 110b, 110c, in which each of the magnetic field sensors is arranged so that its primary sensing direction is aligned with a different axis (e.g., the primary sensing directions of magnetic field sensors 110a, 110b, 110c are aligned orthogonally to one another). For example, magnetic field sensor 110a may have a primary sensing direction of the X-axis. Magnetic field sensor 110b may have a primary sensing direction of the Y-axis, and magnetic field sensor 110c may have a primary sensing direction of the Z-axis. In such a tri-axis configuration, each of the magnetic field sensors 110a, 110b, 110c, may utilize a half-Wheatstone bridge configuration. Such a tri-axis configuration would require a total of eight wires 116—two to provide power to position sensing system 108, and two for each of the three half Wheatstone bridges of magnetic field sensors 110a, 110b, 110c. In another example, only two magnetic field sensors (e.g., magnetic field sensors 110a, 110b) may be utilized to measure six degrees of freedom, with each of magnetic field sensors 110a, 110b having a half-Wheatstone bridge configuration (or a full Wheatstone bridge configuration). In a further example, two magnetic field sensors (e.g., magnetic field sensors 110a, 110b) could be used to measure five degrees of freedom. In such an example, position sensing system 108 may be unable to measure roll. In an additional example, a single magnetic field sensor 110a could use a half Wheatstone bridge to measure five degrees of freedom.

The above examples are merely illustrative and other configurations of magnetic field sensors may be utilized. A system that utilizes three magnetic field sensors 110a, 110b, 110c in a dual-axis, six-degree-of-freedom arrangement, as shown in FIGS. 2A-2C may be beneficial due to an ability to measure six degrees of freedom while requiring only six wires 116. Alternative arrangements may also be used for lighting elements 50 and camera 52. As shown in FIGS. 2A-2C and described above, all of the contact (e.g., solder) pads 57, 117 for wires 56, 116 may be disposed on a single side of substrate 102 (e.g., the first side as shown in FIG. 2A, and described above), which may allow for bonding of wires 56, 116 to substrate 102 in a single manufacturing process without flipping over distal component assembly 100.

Distal component assembly 100 may also include components in addition to or in the alternative to the components described above. For example, distal component assembly 100 also may include additional or alternative sources of lighting and/or additional or alternative imaging components (e.g., additional cameras). Distal component assembly 100 may also include additional types of sensors, such as moisture sensors, temperature sensors, pressure sensors, or other types of sensors, which may be useful during a medical procedure.

Although the magnetic field sensors 110a, 110b, 110c are described above as being TMR sensors, other types of sensors may also be utilized on substrate 102. For example, one or more inductive sensors may be utilized. Inductive sensors may include one or more coils for measuring a magnetic field and determining a positioning and/or orientation of distal tip 44. Any suitable arrangement of inductive sensors may be utilized to measure a desired number of degrees of freedom. For example, inductive sensors may be positioned at least 11 degrees askew from one another (e.g., may be angled relative to a longitudinal axis of distal tip 44).

In some examples, TMR sensors may have lower costs and/or smaller sizes than inductive sensors. An inductive sensor array may require two inductive sensors (which may each be greater than 0.25" long) placed askew from one another, to create an array measuring approximately 0.06-0.08" (e.g., approximately 0.071") by approximately 0.25-0.26" (e.g., approximately 0.255"). A TMR die may have dimensions such as approximately 0.015-0.03" (e.g., approximately 0.024") by approximately 0.01-0.025" (e.g., approximately 0.018"). An array of elements, such as position sensing system 108, may occupy a footprint of approximately 0.01-0.03" (e.g., approximately 0.018") by approximately 0.1-0.2" (e.g., approximately 0.156") if placed in a linear configuration. Because a TMR die and associated elements (e.g., diodes and capacitors) are modular, they may be arranged in various patterns, to, for example, minimize space and/or accommodate other features of distal component assembly 100. For example, as shown in FIG. 2A, magnetic field sensors 110a, 110b, 110c, and diodes 112 may be arranged approximately linearly. For example, as shown in FIG. 2A, one diode 112 may be proximal of magnetic field sensors 110a, 110b, 110c, and one diode 112 may be distal to magnetic field sensors 110a, 110b, 110c. An arrangement of components of distal component assembly 100 may be chosen so as to save space and provide a small footprint and size of substrate 102. Capacitor 114 may be positioned between a proximal end of camera 52 and the contact pads 57 for wires 56. Although TMR sensors may be utilized for distal component assembly 100, the disclosure is not limited to TMR sensors and may include any type of sensor, including those listed above.

To assemble distal component assembly 100, substrate 102 (e.g., multi-layered PCB) may be assembled with magnetic field sensors 110a, 110b, 110c, diodes 112, and capacitor 114 using, for example, a pick-and-place machine. Once in place, magnetic field sensors 110a, 110b, 110c, diodes 112, and capacitor 114 may be wire-bonded to substrate 102 and electrically tested. Thereafter, camera 52 and lighting elements 50 may be held in position using fixturing, and may have their electrical contacts bonded (e.g., at a 90 degree angle) to solder pads of substrate 102. This process of soldering camera 52 and lighting elements 50 may be performed on both sides of substrate 102. Finally, wires 56, cables 58, and wires 116 may be bonded on appropriate sides of substrate 102, via respective contact pads 57, 59, 117. For example, wires 56 for connecting to lighting elements 50 and wires 116 for connecting to position sensing system 108 may be bonded to the first side of substrate 102 in a single step. The above steps and order are merely exemplary. Wires 56, cables 58, and wires 116 may be formed into a single bundle for passing through shaft 42. Additional or alternative steps may be utilized, and different orders of steps may be performed.

Figure 3A:
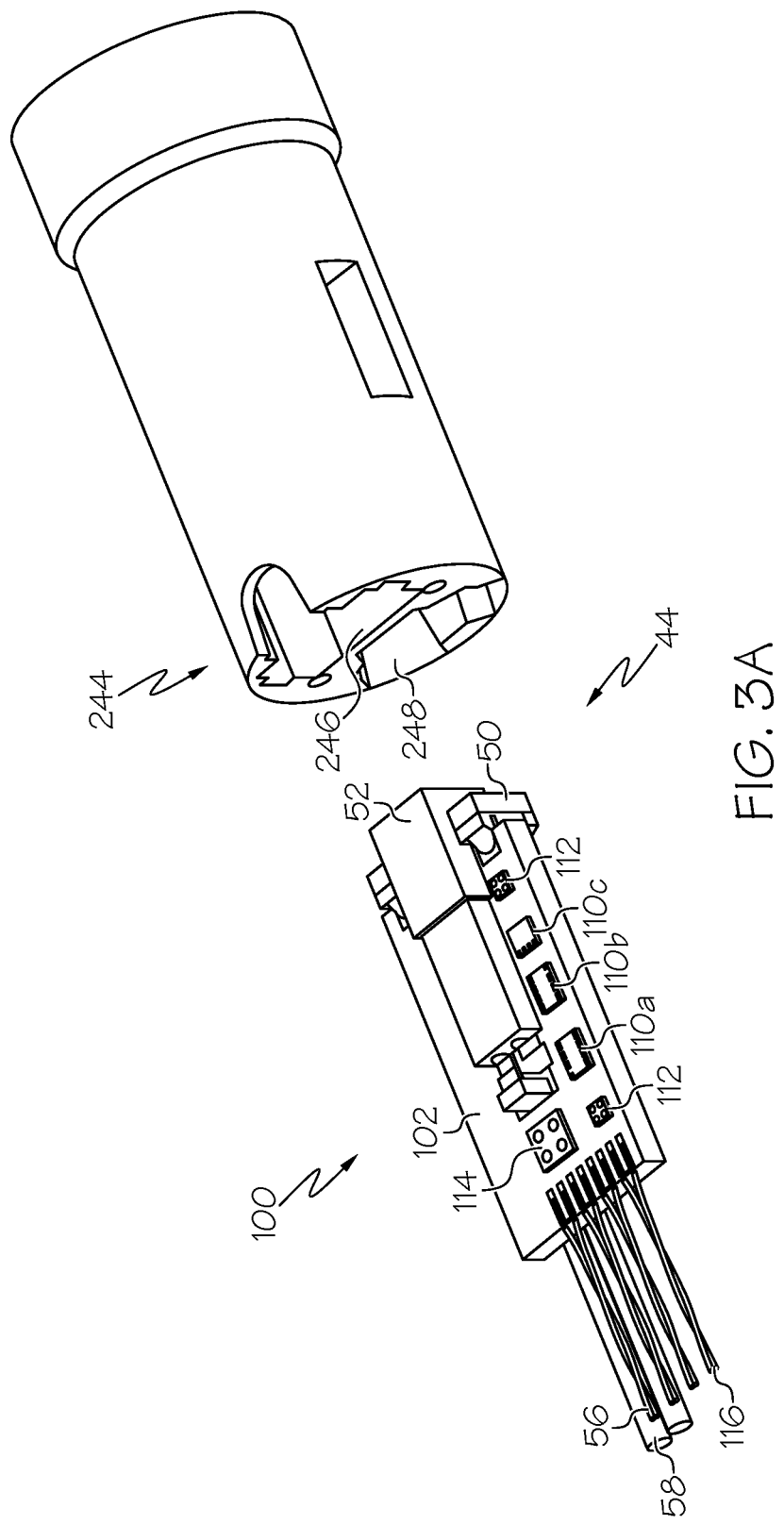
Figure 3D:
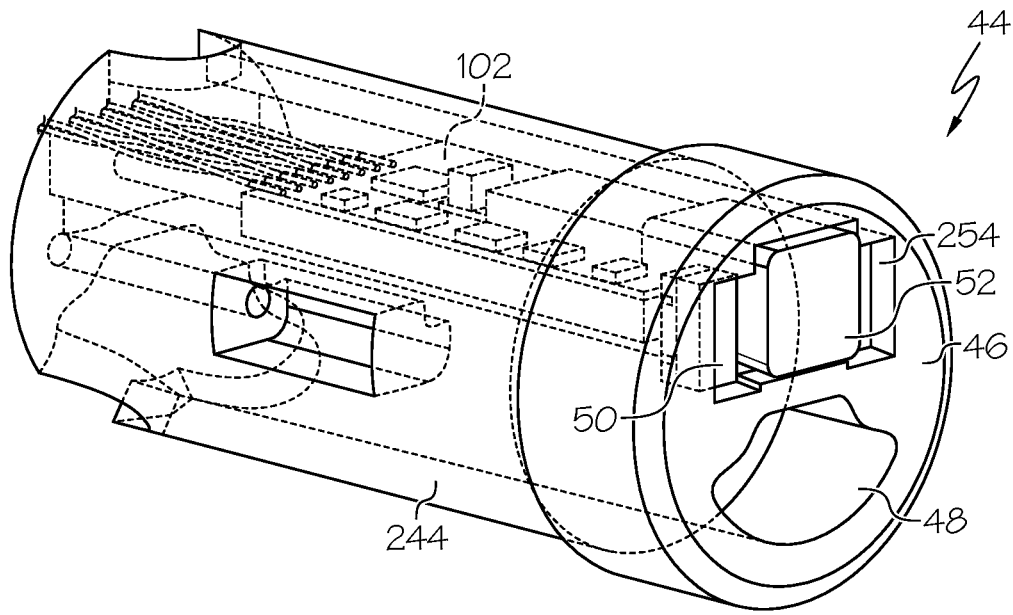
Figure 3E:
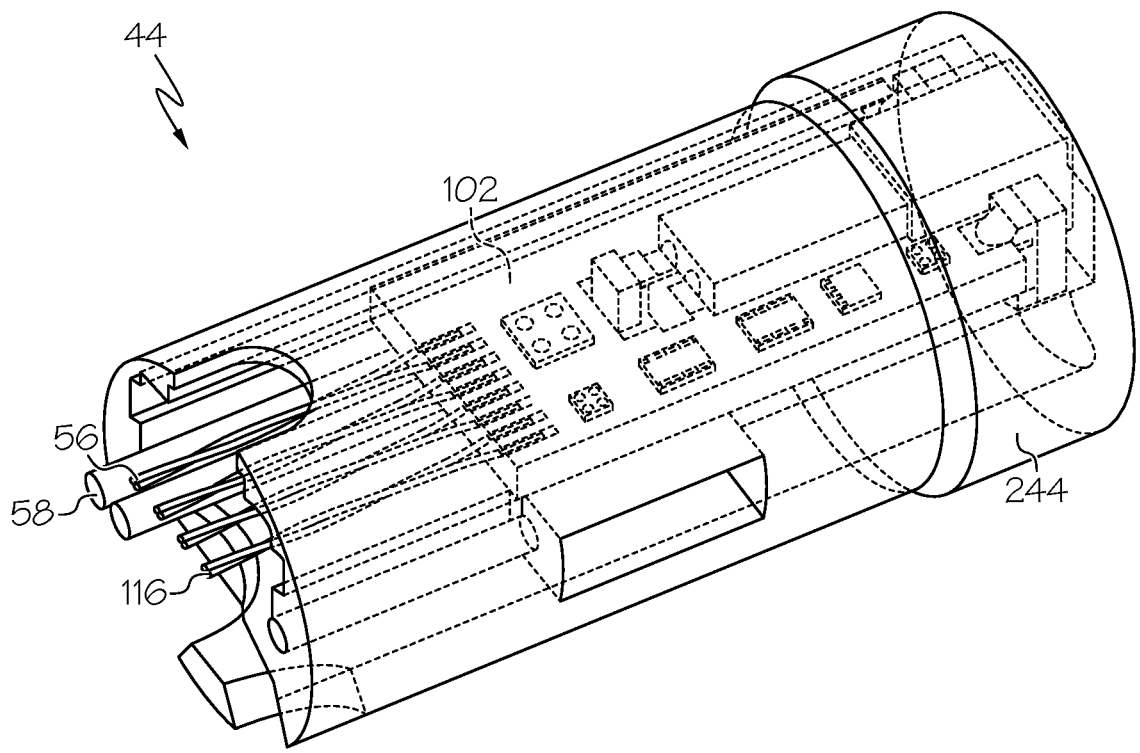
Figure 3F:
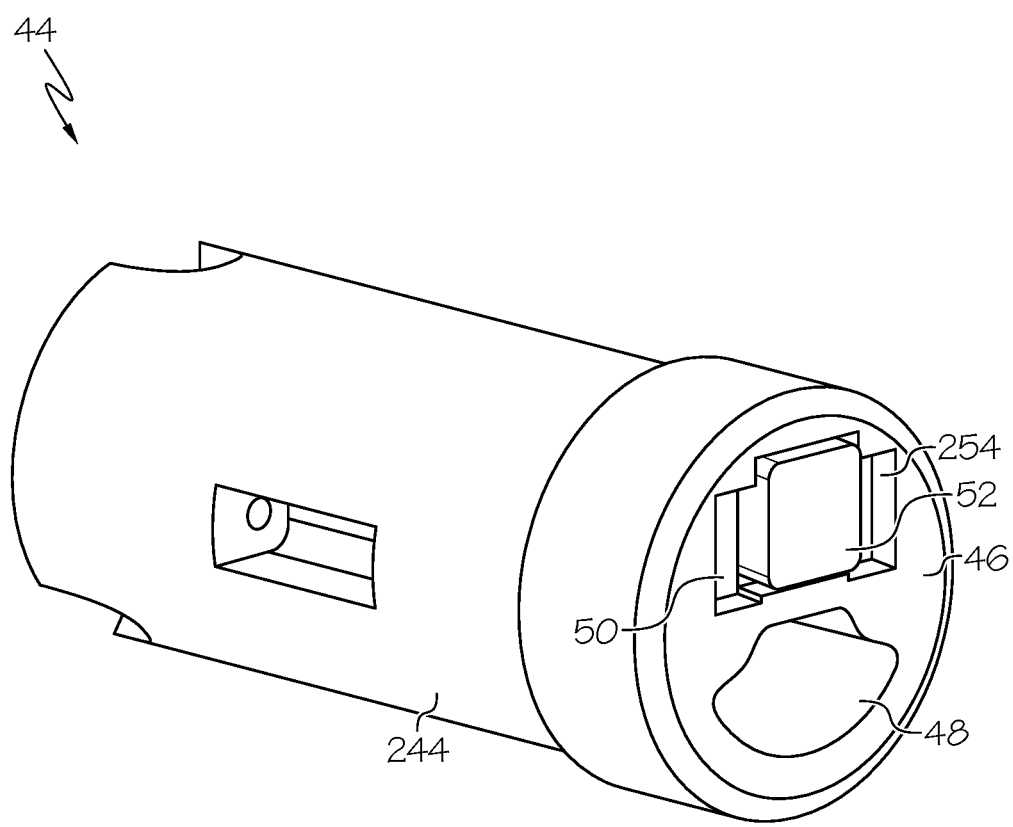

FIGS. 3A-3F show an exemplary distal tip 44, having a distal tip body 244 and distal component assembly 100. FIG. 3A shows distal tip body 244 and distal component assembly 100 before they are assembled together. FIG. 3B shows a cross-sectional view of distal tip 44 (taken along a longitudinal axis of distal tip 44), showing the first side of distal component assembly 100. FIG. 3C shows a detail view of aspects of distal tip body 244 and distal component assembly 100. FIGS. 3D and 3E show perspective views of distal tip 44, with distal tip body 244 having transparent portions. FIG. 3F shows a perspective view of distal tip 44.

Distal tip body 244 may define a distal portion of the working channel, which may terminate distally in working channel opening 48 (see FIGS. 3D and 3F, particularly). Distal tip body 244 may also define a cavity 246. Cavity 246 may extend from a proximal end of distal tip body 244 to a distal end of distal tip body 244. Cavity 246 may be sized and shaped to receive distal component assembly 100. For example, cavity 246 may include a contoured shape (e.g., a contoured surface) having recesses to accommodate camera 52 and lighting elements 50. As shown in FIG. 3B, cavity 246 may have a proximal portion 248 and a distal portion 250. Proximal portion 248 may have a width (a dimension extending across the first and second faces of substrate 102, perpendicularly to the longitudinal axis of substrate 102 and device 10) that is greater than a width of distal portion 250. In other words, distal portion 250 may have a smaller width than proximal portion 248.

Distal portion 250 may terminate in a distal opening 254 (see FIGS. 3D and 3F), a shape of which may be contoured so as to receive camera 52 and lighting elements 50. For example, a surface of distal opening 254 may have a complementary shape or an approximately complementary shape to outer surfaces of camera 52 and lighting elements 50. In other words, a shape of distal opening 254 may serve to align and retain camera 52 and lighting elements 50 in a desired position. A shape of distal opening 254 may also limit the size of margins around camera 52 and lighting elements 50, to allow for easier sealing (as discussed below) of distal opening 254 and less opportunity for fluid ingress/egress through distal opening 254. In one example, because camera 52 may extend radially outward from the first face further than lighting elements 50, a first side of distal opening 254 (a side toward the top of FIGS. 3D and 3F) may have a central portion that extends further radially outward than laterally outer portions of distal opening 254, to accommodate shapes of camera 52 and lighting elements 50. In the example, because lighting elements 50 may extend radially outward from the second face further than camera 52, a second side of distal opening 254 (opposite of the first side and toward the bottom of FIGS. 3D and 3F) may have laterally outer portions that extend further radially outward than a central portion, to accommodate shapes of camera 52 and lighting elements 50.

Symmetrical shoulder portions 252 may define interfaces between proximal portion 248 and distal portion 250. Shoulder portions 252 may define a distal surface of cavity 246 between proximal portion 248 and distal portion 250. As shown in FIGS. 2A-2C, and described above, substrate 102 may extend width-wise beyond each of lighting elements 50, in a symmetrical fashion. Distal portion 250 may be wide enough to accommodate camera 52 and lighting elements 50 but may be narrower (smaller) than substrate 102. Proximal portion 248 may be wide enough to accommodate substrate 102. To assemble distal tip 44, a distal end 104 of distal component assembly 100 may be inserted into a proximal opening of cavity 246. Camera 52 and lighting elements 50 may pass into distal portion 250 of cavity 246, such that camera 52 and lighting elements 50 are at least partially received within distal portion 250 of cavity 246. On either side of lighting elements 50, substrate 102 may abut shoulder portions 252. Thus, shoulder portions 252 may act as stops that serve to help align distal component assembly 100 in a desired position and to help inhibit distal component assembly 100 from being advanced distally beyond a desired position. As shown in FIG. 3C, a width E of shoulder portion 252 may abut either side of substrate 102. Width E may be approximately 0.005" or larger. For example, width E may be approximately 0.005" to approximately 0.010". When distal component assembly 100 is positioned within cavity 246, it may incidentally be positioned slightly asymmetrically, so the width E may be slightly different on either side of substrate 102.

When assembled, as shown in FIG. 3B, a length of distal tip 44, from a proximal end of distal tip body 244 to a distal end of camera 52 (which may extend distally past a distal end of distal tip body 244) may be approximately 0.300-0.400". For example, the length C of distal tip 44 may be approximately 0.330". A width D (e.g., a diameter) of distal tip 44 at a widest point may be approximately 0.100-0.250". For example, distal tip 44 may have a width at a widest point of approximately 0.155", approximately 0.197", or approximately 0.231". Each of the dimensions provided herein is merely exemplary, and any other suitable dimension may be chosen. For example, different widths may be utilized for different types of devices (e.g., a duodenoscope may have a larger width than a bronchoscope).

To assemble distal component assembly 100 and distal tip body 244, a distal end 104 of distal component assembly 100 may be inserted into a proximal opening of cavity 246. Distal component assembly 100 may be advanced distally until an edge of substrate 102 abuts shoulder portion 252. An epoxy adhesive may be applied to camera 52 and/or lighting elements 50 to help seal distal opening 254 from fluid ingress/egress and to help hold distal component assembly 100 (including substrate 102) in place. Other techniques may also be used to secure distal component assembly 100. For example, other types of adhesive, screws, pins, crimps, snap-fit, or other features may be used to secure distal component assembly 100 to distal tip body 244. Such securing features may be, for example, used at a proximal end of cavity 246, a distal end of cavity 246, or via openings extending from an outer surface of distal tip body 244 (e.g., a radially outer surface of distal tip body 244) to cavity 246. Overmolding or similar techniques may also be used to secure distal component assembly 100 to distal tip body 244 or to secure elements of distal component assembly 100 to substrate 102. Overmolding may also be used to form distal tip 44 around distal component assembly 100, without use of a distal tip body 244. For example, distal component assembly 100 may be loaded into an injection mold, and a material may be injected into the mold in order to form distal tip 44. For example, a portion of distal tip 44 may be molded directly onto substrate 102, camera 52, lighting elements 50, camera capacitor 54, magnetic sensors 110a, 110b, 110c, diodes 112, and/or capacitor 114 and combined with other preformed or overmolded components to form distal tip 44. Elements of distal tip 44, such as distal tip body 244, may be constructed using 3D printing.

In alternative examples, substrate 102 may include a flexible circuit board that is manufactured with substrate 102 in a flat configuration and then folded prior to insertion into distal tip body 244. In examples including a flexible circuit board, lighting elements 50 may be positioned on a different plane of substrate 102 than camera 52. Components may be surface mounted on substrate 102 and then bent by an angle (e.g., by approximately 90 degrees) to face forwards (distally) or in any other direction. In further alternatives, instead of components (such as lighting elements 50, camera 52, camera capacitor 54, magnetic sensors 110a, 110b, 110c, diodes 112, or capacitor 114) being mounted on substrate 102 (as shown in FIGS. 2A-3E and described above), components may be embedded in substrate 102 according to any suitable methods.

Distal tip 44 may be further assembled by performing steps such as connecting articulation wires to distal tip 44 and assembling the distal tip 44 onto shaft 42. Wires 56, 116 and cables 58 may be backfed through shaft 42. Handle portion 12 may include connections for connecting to proximal ends of wires 56, 116 and cables 58. For example, handle portion 12 may include a circuit board, such as a printed circuit board, having connections for the wires. Such connections may include six passive connections for the wires 116 connected to position sensing system 108 (including magnetic field sensors 110a, 110b, 110c). Alternative numbers of connections may be utilized, as appropriate, depending on a configuration of distal component assembly 100. Umbilicus 30 may include conductors (e.g., wires) for carrying power and/or signals from distal component assembly 100. For example, umbilicus 30 may include six wires 116 in twisted pairs to route power and/or signals to and from position sensing system 108 through umbilicus 30.

Once assembled, device 10 may be used to perform a medical procedure on a subject. For example, device 10 may be inserted into a body lumen (e.g., an airway) of a subject. During the procedure, an external device may be used to generate a magnetic field near the subject. For example, the external device may be positioned on a table or other surface near the subject (e.g., near the part of the body where the body lumen is located). During the procedure, position sensing system 108 (including magnetic field sensors 110a, 110b, 110c) may transmit signals through shaft 42, to handle portion 12, and through umbilicus 30 to a controller. The signals from position sensing system 108 may indicate a position and/or orientation of distal tip 44 within the body. Such position and/or orientation information may be fused with imaging (e.g., 3D imaging) performed before the procedure. Information from position sensing system 108 may provide an operator with information about anatomy near device 10, which camera 52 alone may be unable to visualize (including anatomy outside of the body lumen in which device 10 is disposed). Furthermore, pre-procedure images may be used to automatically segment a mesh of the anatomy so as to provide a map (e.g., a 3D map) to track device 10 in real time. Such real-time tracking may decrease the amount of time, skill, and/or effort required to reach a target anatomy. In the absence of pre-procedure images, EM sensors may enable software to track a position of device 10 and movements of device 10 in order to generate a map (e.g., a 3D map) in real time, during the procedure. The generated map may guide device 10 (and any EM-enabled accessories) through the subject's anatomy.

In an alternative, distal tip 44 may include elements to generate a magnetic field, and an external device may include elements that measure the magnetic field and determine positioning and/or orientation of distal tip 44. For example, distal tip 44 may include one or more coils (e.g., solenoids). Circuitry element(s), such as wire(s), circuit board(s), and/or one or more other component(s) mounted on circuit board(s) may transmit current through the coil(s). The coil(s) may thus generate a magnetic field. The external device may include one or more sensors (including, for example, any of the types of sensors described above) or assemblies for measuring the magnetic field emitted by the coil(s). Measurements from the sensors or assemblies of the external device may be used (e.g. by a controller) to determine a position of distal tip 44.

Any methods or portions of methods described in this disclosure may be performed by one or more processors of a computer system (e.g., of a controller). The one or more processors may be configured to perform such methods by having access to instructions (e.g., software or computer-readable code) that, when executed by the one or more processors, configure and/or cause the one or more processors to perform the methods. Such instructions may be stored in a memory of the computer system.

Instructions executable by one or more processors may also be stored on a non-transitory computer-readable medium. Therefore, whenever a computer-implemented method is described in this disclosure, this disclosure shall also be understood as describing a non-transitory computer-readable medium storing instructions that, when executed by one or more processors of a computer system, configure and/or cause the one or more processors to perform the computer-implemented method. Examples of non-transitory computer-readable media include RAM, ROM, solid-state storage media (e.g., solid state drives), optical storage media (e.g., optical discs), and magnetic storage media (e.g., hard disk drives). A non-transitory computer-readable medium may be part of the memory of a computer system or separate from any computer system.

A computer system may include one or more computing devices. If a computer system includes a plurality of processors, the plurality of processors may be included in a single computing device or distributed among a plurality of computing devices. A processor may be a central processing unit (CPU), a graphics processing unit (GPU), or another type of processing unit. The term "computational device," as used in this disclosure, is interchangeable with "computing device." An "electronic storage device" may include any of the non-transitory computer-readable media described above.

While principles of this disclosure are described herein with the reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical assembly, comprising:
   a distal tip body at a distal tip of a medical device, the distal tip body including a cavity, wherein the cavity has a single distal opening on a distal face of the distal tip body;
   a substrate disposed in the cavity of the distal tip body;
   a position sensing system, including a magnetic field sensor mounted to the substrate, wherein the magnetic field sensor is configured to provide a signal that indicates a position or orientation of the distal tip of the medical device;
   at least one camera mounted to the substrate; and
   at least one lighting element mounted to the substrate;
   wherein a surface of the single distal opening of the cavity is contoured to outer surfaces of the at least one camera and the at least one lighting element such that a shape of the single distal opening of the cavity matches with a shape defined by the outer surfaces of the at least one camera and the at least one lighting element.

2. The assembly of claim 1, wherein the magnetic field sensor includes a first magneto-resistive ("MR") sensor, and wherein the position sensing system further includes a second MR sensor and a third MR sensor.

3. The assembly of claim 2, wherein the first MR sensor has a first primary sensing direction, wherein the second MR sensor has a second primary sensing direction, wherein the third MR sensor has a third primary sensing direction, wherein the first MR sensor and the second MR sensor are arranged so that each of the first primary sensing direction and the second primary sensing direction is approximately parallel with a longitudinal axis of the substrate.

4. The assembly of claim 3, wherein the third MR sensor is arranged such that the third primary sensing direction is transverse to the longitudinal axis of the substrate.

5. The assembly of claim 2, wherein the position sensing system is configured to measure at least five degrees of freedom.

6. The assembly of claim 2, wherein the first MR sensor, the second MR sensor, and the third MR sensor collectively include at least one Wheatstone bridge configuration.

7. The assembly of claim 2, further comprising six wires in electrical connection with the position sensing system, and two wires in electrical connection with the at least one lighting element.

8. The assembly of claim 7, wherein each of the six wires in electrical connection with the position sensing system and each of the two wires in electrical connection with the at least one lighting element is connected to a first side of the substrate.

9. The assembly of claim 1, wherein the cavity extends from a proximal end of the distal tip body to a distal end of the distal tip body, and wherein the cavity receives an entirety of the substrate.

10. The assembly of claim 9, wherein the cavity includes a proximal portion and a distal portion, wherein the distal portion of the cavity has a smaller width than the proximal portion of the cavity, and wherein the width is measured in a direction that is perpendicular to a longitudinal axis of the medical device and across a face of the substrate.

11. The assembly of claim 10, wherein distal portions of the at least one camera and the at least one lighting element that extend distally from a distal edge of the substrate are received within the distal portion of the cavity.

12. The assembly of claim 10, wherein the cavity defines a shoulder portion extending between the proximal portion of the cavity and the distal portion of the cavity, and wherein a distal edge surface of the substrate contacts the shoulder portion.

13. The assembly of claim 9, wherein a surface of an entirety of the cavity extending from a proximal end of the distal tip body to a distal end of the distal tip body, including the surface defining the single distal opening of the cavity, is contoured outward of the at least one camera and the at least one lighting element such that a shape of the entirety of the cavity corresponds to the shape of the at least one camera and the at least one lighting element.

14. A medical assembly, comprising:
a distal tip body at a distal tip of a medical device, wherein the distal tip body defines a unitary cavity extending from a proximal end of the distal tip body to a distal end of the distal tip body, the unitary cavity having a single distal opening on a distalmost face of the distal end of the distal tip body; and
a substrate entirely disposed in the unitary cavity, the substrate having mounted thereto:
a magnetic field sensor configured to provide a signal that indicates a position or orientation of the distal tip of the medical device;
at least one camera; and
at least one lighting element;
wherein a surface of the unitary cavity is contoured to outer surfaces of the at least one camera and the at least one lighting element such that a shape of the unitary cavity matches with a shape defined by the outer surfaces of the at least one camera and the at least one lighting element.

15. The assembly of claim 14, wherein the unitary cavity includes a proximal portion and a distal portion terminating at the single distal opening, wherein the distal portion of the unitary cavity, including the single distal opening, has a smaller width than the proximal portion of the unitary cavity, wherein the width is measured in a direction that is perpendicular to a longitudinal axis of the medical device and across a face of the substrate, and wherein a distal portion of each of the at least one camera and the at least one lighting element that extends distally from a distal edge of the substrate is received within the distal portion of the unitary cavity.

16. A medical assembly, comprising:
a distal tip body at a distal tip of a medical device, wherein the distal tip body defines (a) a distal portion of a working channel terminating at a working channel opening on a distalmost face of the distal tip body; and (b) a unitary cavity, the unitary cavity being separate from the distal portion of the working channel and extending from a proximal end of the distal tip body to a distal end of the distal tip body, the unitary cavity terminating at a single distal opening on the distalmost face of the distal end of the distal tip body;
a substrate entirely disposed in the unitary cavity;
a magnetic field sensor mounted to the substrate, wherein the magnetic field sensor is configured to provide a signal that indicates a position or orientation of the distal tip of the medical device;
a camera mounted to the substrate; and
a lighting element mounted to the substrate;
wherein a portion of the camera that extends distally from a distal edge of the substrate is received by the single distal opening;
wherein the substrate includes a plurality of contact pads disposed on a first side of the substrate, wherein at least a first of the plurality of contact pads is configured to provide an electrical connection between (a) a first conductor and (b) the magnetic field sensor, and wherein at least a second of the plurality of contact pads is configured to provide an electrical connection between (c) a second conductor and (d) the camera or the lighting element.

17. The medical assembly of claim 1,
wherein the substrate defines a longitudinal axis, wherein, relative to the longitudinal axis, the at least one camera extends a greater radial distance in a first direction from a first face of the substrate than the at least one lighting element does, and
wherein a first side of the single distal opening of the cavity has a first portion and a second portion, wherein the first side is in the first direction relative to the longitudinal axis, wherein the first portion extends a greater radial distance from the longitudinal axis than the second portion does, wherein the first portion accommodates the at least one camera, and wherein the second portion accommodates the at least one lighting element.

18. The medical assembly of claim 17,
wherein, relative to the longitudinal axis, the at least one lighting element extends a greater radial distance in a second direction from a second face of the substrate than the at least one camera does, and
wherein a second side of the single distal opening of the cavity has a third portion and a fourth portion, wherein the second side is in the second direction relative to the longitudinal axis, wherein the third portion extends a greater distance from the longitudinal axis than the fourth portion does, wherein the third portion accommodates the at least one lighting element, and wherein the fourth portion accommodates the at least one camera.

19. The medical assembly of claim 16, wherein the unitary cavity includes a proximal portion and a distal portion terminating at the single distal opening, wherein a width of the distal portion of the unitary cavity is smaller than a width of the substrate to prevent the substrate from being received by the distal portion of the unitary cavity, and prevents a distal portion of the medical assembly that extends distally from the distal edge of the substrate from being advanced distally past a defined position.

20. The medical assembly of claim 14, wherein the distalmost face of the distal tip body further defines a working channel opening, separate from the single distal opening of the unitary cavity.

\* \* \* \* \*